(12) United States Patent
Suzuki

(10) Patent No.: US 6,767,344 B2
(45) Date of Patent: Jul. 27, 2004

(54) DISPOSABLE WEARING ARTICLE

(75) Inventor: Seiji Suzuki, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 310 days.

(21) Appl. No.: 09/964,682

(22) Filed: Sep. 27, 2001

(65) Prior Publication Data

US 2002/0040215 A1 Apr. 4, 2002

(30) Foreign Application Priority Data

Sep. 29, 2000 (JP) ........................................ 2000-300203

(51) Int. Cl.[7] .............................................. A61F 13/15
(52) U.S. Cl. ........................... 604/385.28; 604/385.24; 604/385.25; 604/385.26; 604/385.27; 604/396
(58) Field of Search ...................... 604/385.01, 385.22, 604/385.24–385.28, 396

(56) References Cited

U.S. PATENT DOCUMENTS

| | | | |
|---|---|---|---|
| 2,575,164 A | | 11/1951 | Donovan |
| 5,558,660 A | * | 9/1996 | Dreier ................... 604/385.19 |
| 5,569,227 A | | 10/1996 | Vandemoortele et al. |
| 5,575,785 A | * | 11/1996 | Gryskiewicz et al. .. 604/385.28 |
| 5,836,930 A | | 11/1998 | Lantz et al. |
| 5,904,675 A | | 5/1999 | Laux et al. |
| 6,102,892 A | * | 8/2000 | Putzer et al. .......... 604/385.01 |
| 6,103,952 A | | 8/2000 | Coles et al. |
| 6,121,510 A | | 9/2000 | Sauer |

FOREIGN PATENT DOCUMENTS

| | | |
|---|---|---|
| EP | 0 847 739 A2 | 6/1998 |
| EP | 0 847 739 A3 | 3/1999 |
| GB | 2 259 441 A | 3/1993 |
| JP | 4-354948 | 12/1992 |

OTHER PUBLICATIONS

European search report mailed Feb. 5, 2002.

* cited by examiner

Primary Examiner—John J. Calvert
Assistant Examiner—Jacqueline Stephens
(74) Attorney, Agent, or Firm—Butzel Long (57) ABSTRACT

A disposable wearing article that includes a substantially liquid-impervious leak-barrier cuff associated with a waist-opening, which has a fixed end portion lying on a side of one longitudinal end portion of an article, a free end portion extending from the fixed end portion toward a crotch region and fixed side portions lying on the transversely opposite side edge portions of the article. A rising fulcrum zone of the leak-barrier cuff lies in a substantially non-contractible region of the article extending between the elastic member associated with the waist-opening and elastic members associated with leg-openings.

5 Claims, 11 Drawing Sheets

DISPOSABLE WEARING ARTICLE

BACKGROUND OF THE INVENTION

This invention relates to a disposable wearing article adapted to absorb and to hold excretion discharged thereon.

Japanese Patent Application Publication No. 1992-354948A describes a disposable pants comprising a liquid-pervious topsheet, a liquid-impervious backsheet and a liquid-absorbent core disposed between the top- and backsheets, configuring a front waist region and a rear waist region opposed to each other and a crotch region extending between these waist regions so that the front and rear waist regions may be bonded together along side edge portions thereof to define a waist-opening and a pair of leg-openings.

In the pants disclosed in the Publication, the elastic member comprising a plurality of elastic elements being stretchable in the waist-surrounding direction is attached under tension to the peripheral edge portion of the waist-opening. Similarly, the elastic members each comprising a plurality of elastic elements being stretchable in the leg-surrounding direction are attached under tension to the peripheral edge portions of the respective leg-openings. The peripheral edge portion of the waist-opening is provided with the leak-barrier cuff exclusively for the waist-opening extending in the waist-surrounding direction. This leak-barrier cuff has the fixed end portion lying on the peripheral edge portion of the waist-opening and bonded to the pants, the free end portion extending from the fixed end portion toward the crotch region and fixed side portions lying on the transversely opposite side edge portions of the front and rear waist regions and bonded to the pants. The elastic member being stretchable in the waist-surrounding direction is attached with tension to the fixed side portions. With this leak-barrier cuff, the free end portion rises on the topsheet to form the barrier as the elastic member associated with this leak-barrier cuff contracts.

In the case of the pants disclosed in the Publication, the fixed side portions of the leak-barrier cuff are placed upon the elastic member associated with the waist-opening and the rising fulcrum zone of the leak-barrier cuff lies adjacent the elastic member associated with the waist-opening. Such arrangement is disadvantageous in that the fixed end portion as well as the free end portion of the leak-barrier cuff contract in the waist-surrounding direction as the elastic member associated with the waist-opening contracts. Contraction of the free end portion of the leak-barrier cuff generates a plurality of creases or gathers. As a result, the free end portion partially rises on the topsheet and partially collapses toward the topsheet. The parts collapsed toward the topsheet can not function as the barrier and there is an apprehension that excretion discharged on the pants might flow beyond these collapsed parts of the leak-barrier cuff and leak out from the peripheral edge portion of the waist-opening.

SUMMARY OF THE INVENTION

An object of this invention is to provide a disposable wearing article configured so that a free end portion of a leak-barrier cuff associated with a waist-opening is not collapsed even partially toward a topsheet and reliably functions as a barrier adapted to prevent excretion from leaking.

According to this invention, there is provided a disposable wearing article comprising a liquid-pervious topsheet, a liquid-impervious backsheet, a liquid-absorbent core, configuring a front waist region, a rear waist region and a crotch region extending between these front and rear waist regions, longitudinally opposite end portions extending in parallel to each other in a first direction across the front and rear waist regions, respectively, transversely opposite side edge portions extending between the longitudinally opposite end portions in a second direction, elastic members being stretchable in the first direction attached under tension to the longitudinally opposite end portions so as to be associated with a waist-opening, elastic members being stretchable in the second direction attached with tension to the transversely opposite side edge portion in the crotch region so as to be associated with respective leg-openings, and a substantially liquid-impervious leak-barrier cuff associated with the waist-opening extending in the first direction across at least the rear waist region of the front and rear waist regions.

According to this invention the leak-barrier cuff has a fixed end portion lying adjacent one longitudinal end portion of the article, a free end portion extending the fixed end portion toward the crotch region and fixed side portions lying on respective the side edge portions wherein elastic member being stretchable in the first direction is attached under tension to the free end portion so that the free end portion may be biased by the elastic member to rise on the topsheet and a rising fulcrum zone of the leak-barrier cuff may lie in a substantially non-contractible region of the article extending between the elastic member associated with the waist-opening and the elastic member associated with the leg-openings.

According to one embodiment of this invention, a substantially liquid-impervious cover sheet having a central opening which is relatively long in the second direction is provided on the outer surface of the topsheet and bonded to the longitudinal opposite end portions as well as to the transversely opposite side edge portions and the leak-barrier cuff extends on the outer surface of the cover sheet in the first direction so that the free end portion may form a barrier rising on the cover sheet.

According to another embodiment of this invention, the opening of the cover sheet extends across the crotch region and further extends into the front and rear waist regions so that the free end portion of the leak-barrier cuff may extend above the opening in the front and rear waist regions.

According to still another embodiment of this invention, the leak-barrier cuff is defined by a part of the cover sheet extending outward from the longitudinally opposite end portions of the article in the second direction and folded back along the longitudinally opposite end portion toward the outer surface of the cover sheet.

According to a further embodiment of this invention, the leak-barrier cuff is defined by a part of the backsheet extending outward from the longitudinally opposite end portions of the article in the second direction and folded back along the longitudinally opposite end portions toward the outer surface of the topsheet.

According to a further additional embodiment of this invention, the rising fulcrum zone of the leak-barrier cuff is spaced apart from the elastic member associated with the waist-opening by a dimension of 5~15 mm.

According to a further alternative embodiment of this invention, the rising fulcrum zone of the leak-barrier cuff lies in the vicinity of the longitudinal end of the core extending between the transversely opposite side edge portions of the article.

DETAILED DESCRIPTION OF THE PREFERRED EMBODIMENTS

Details of a disposable wearing article according to this invention will be more fully understood from the description given hereunder with reference to the accompanying drawings.

Figure 1:
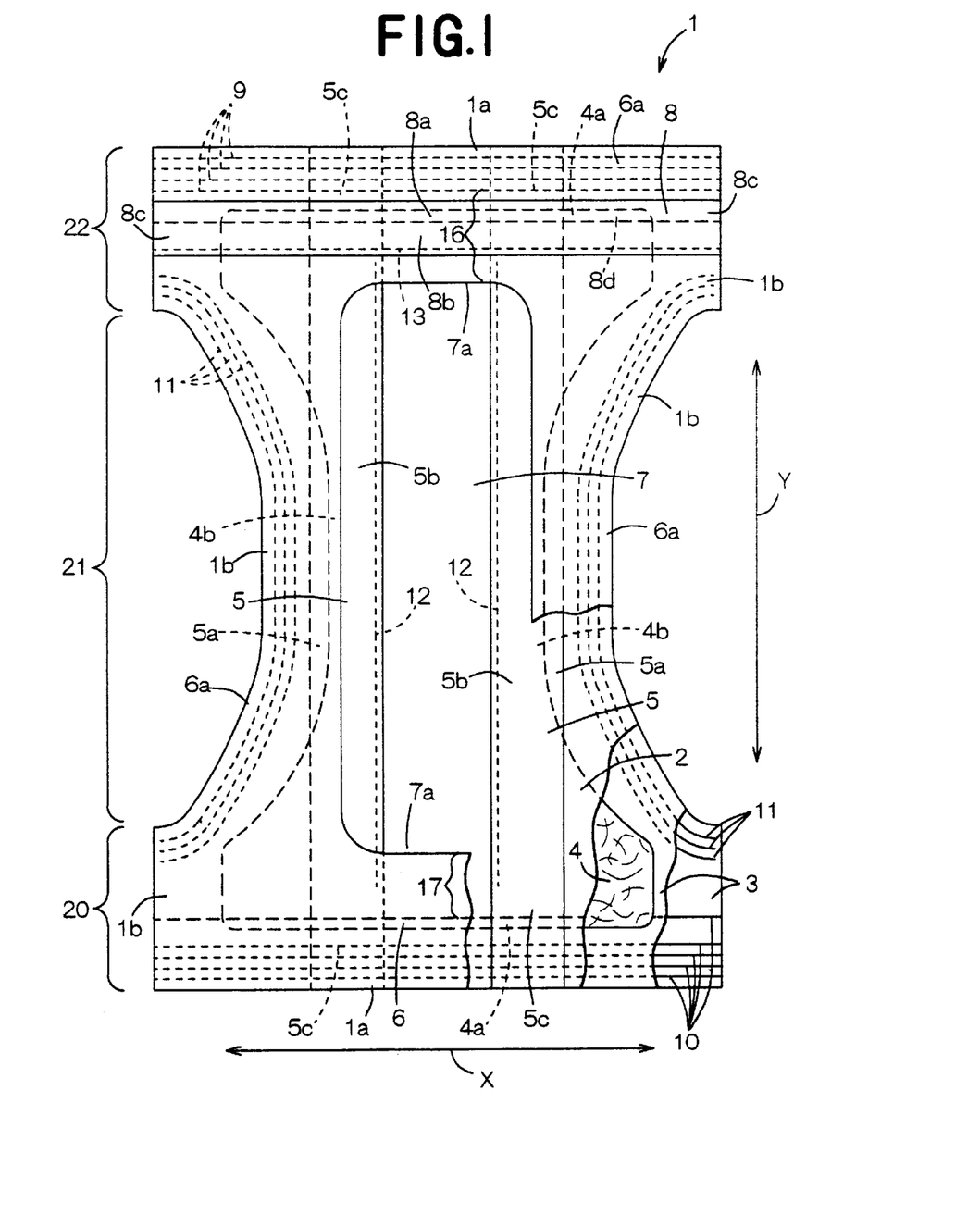
FIG. 1 is a plan view showing a diaper before shaped into a pants-type diaper as partially broken away.
Figure 2:
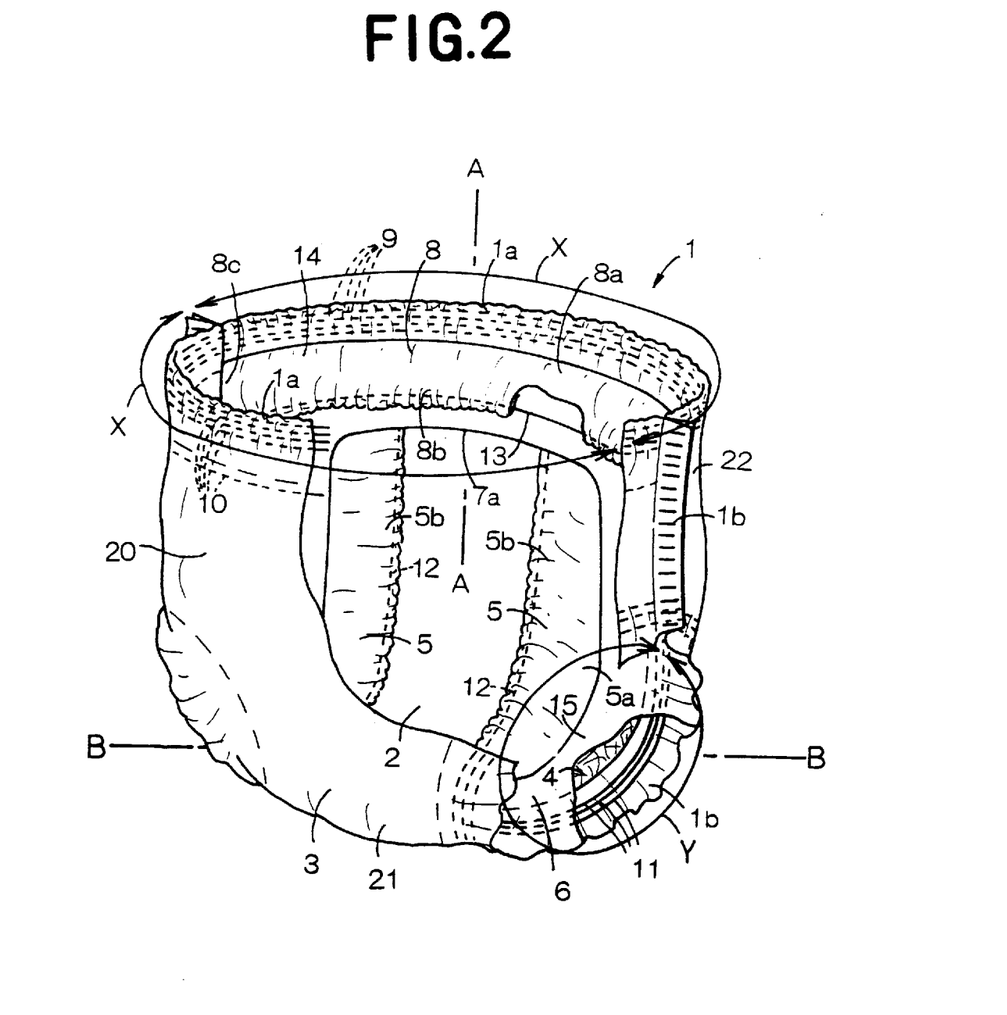
FIG. 2 is a perspective view showing the diaper shaped in the pants-type diaper as partially broken away.

FIG. 1 is a plan view showing a diaper 1 before shaped into a pants-shape as partially broken away and FIG. 2 is a perspective view showing the diaper 1 shaped into such pants-type diaper. Referring to FIG. 1, a transverse direction is indicated by an arrow X and a longitudinal direction is indicated by an arrow Y Referring to FIG. 2, a waist-surrounding direction is indicated by an arrow X and a leg-surrounding direction is indicated by an arrow Y. The transverse direction as well as the waist-surrounding direction correspond to a first direction and the longitudinal direction as well as the leg-surrounding direction correspond to a second direction. The expression used herein "inner surfaces" of top- and backsheets 2, 3 and a cover sheet 6 should be understood to be the surfaces thereof facing a core 4 and the expression used herein "outer surfaces" of these sheets 2, 3, 6 should be understood to be the surfaces thereof not facing the core 4.

The diaper 1 comprises a liquid-pervious topsheet 2, a liquid-impervious backsheet 3, a liquid-absorbent core 4 disposed between the top- and backsheets 2, 3 and entirely covered with and bonded to tissue paper (not shown), a pair of substantially liquid-impervious leak-barrier cuffs 5 associated with leg-openings, the cover sheet 6 being substantially liquid-impervious and having a central opening 7 of a substantially rectangular shape extending in the longitudinal direction and a substantially liquid-impervious leak-barrier cuff 8 associated with a waist-opening. The top-and backsheets 2, 3, the cover sheet 6 and the leak-barrier cuffs 5, 8 are non-stretchable. The core 4 is bonded to inner surfaces of the top- and backsheets 2, 3, respectively, with the core 4 covered by a liquid-diffusion sheet such as tissue paper.

As seen in FIG. 1, the diaper 1 is composed, in the longitudinal direction, a front waist region 20, a rear waist region 22 and a crotch region 21 extending between these waist regions 20, 22, wherein the diaper 1 is contoured by longitudinally opposite end portions 1a extending in parallel to each other in the transverse direction and transversely opposite side edge portions 1b extending in the longitudinal direction. In the crotch region 21, the side edge portions 1b curve inward in the transverse direction of the diaper 1 to describe circular arcs.

Elastic members 9, 10 each comprising a plurality of elastic elements being stretchable in the transverse direction are attached under tension to the longitudinally opposite end portions 1a, respectively, so as to be associated with the waist-opening. In the crotch region 21, elastic members 11 each comprising a plurality of elastic elements being stretchable in the longitudinal direction are attached under tension to the transversely opposite side edge portions 1b so as to be associated with the respective leg-openings.

The pair of the leak-barrier cuffs 5 associated with the leg-openings are attached to the respective side edge portions 1b of the diaper and extend in the longitudinal direction. The cover sheet 6 is attached to the outer surface of the topsheet 2. The leak-barrier cuff 8 associated with the waist-opening is attached to the outer surface of the cover sheet 6 in the rear waist region 22 and extends in the transverse direction.

The leak-barrier cuffs 5 have fixed side edge portions 5a extending in the longitudinal direction in the vicinity of transversely opposite side edges 4b of the core 4, free side edge portions 5b being contiguous to the respective fixed side edge portions 5a and normally biased to rise on the topsheet 2 and fixed longitudinally opposite end portions 5c collapsed inward in the transverse direction of the diaper 1 and bonded to the topsheet 2 in such collapsed state. Elastic members 12 being stretchable in the longitudinal direction are attached under tension to the respective free side edge portions 5b. These elastic members 12 are covered with parts of the respective free side edge portions 5b. Of the leak-barrier cuffs 5, the fixed side edge portions 5a are firmly bonded to the outer surface of the topsheet 2 in the vicinity of the respective side edges 4b of the core 4 (See FIG. 4) and the fixed side edge portions 5c are firmly bonded to the outer surface of the topsheet 2 in the front and rear waist regions 20, 22 of the diaper 1.

The cover sheet 6 covers the end portions 1a as well as the side edge portions 1b and the fixed side edge portions 5a as well as the fixed end portions 5c of the leak-barrier cuffs 5. Specifically, the cover sheet 6 has its inner surface firmly bonded to the end portions 1a and the side edge portions 1b of the diaper. The opening 7 of the cover sheet 6 extends across a substantially entire area of the crotch region 21 and further extends slightly into the front and rear waist regions 20, 22.

The leak-barrier cuff 8 has a fixed end portion 8a lying adjacent the end portion 1a of the rear waist region 22, a free end portion 8b extending the fixed end portion 8a toward the crotch region 21 and fixed side portions 8c lying on the side edge portions 1b of the rear waist region 22 and extending in the longitudinal direction. Of the leak-barrier cuff 8, the fixed end portion 8a and the fixed side portions 8c are firmly bonded to the outer surface of the cover sheet 6. An elastic member 13 being stretchable in the transverse direction is attached under tension to the free end portion 8b. The free end portion 8b is normally biased by contraction of the elastic member 13 to rise on the topsheet 2. The elastic member 13 is covered with a part of the free end portion 8b.

The diaper 1 may be shaped from the state shown in FIG. 1 into the pants-shape shown in FIG. 2 by bonding the front and rear waist regions 20, 22 intermittently along the transversely opposite side edge portions 1b thereof. With the diaper 1 shaped into the pants-shape in this manner, a waist-opening 14 and a pair of leg-openings 15 are defined. Of the diaper 1, the longitudinally opposite end portions 1a define the peripheral edge portion 1a of the waist-opening 14 and the transversely opposite side edge portions 1b in the crotch region 21 define peripheral edge portions 1b of the respective leg-openings 15. The elastic members 9, 10 associated with the waist-opening extend along the peripheral edge portion 1a of the waist-opening 14 in the waist-surrounding direction. The elastic members 11 associated with the leg-openings extends along the peripheral edge portions 1b of the respective leg-openings 15 in the leg-surrounding direction. Of the diaper 1, the leak-barrier cuffs 5 extend along the peripheral edge potions 1b of the respective leg-openings 15 and the leak-barrier cuff 8 extends along the peripheral edge portion 1a of the waist-opening 14 in the rear waist region 22.

In the diaper 1, contraction of the elastic members 9, 10, 11 causes the peripheral edge portion 1a of the waist-opening 14 as well as the peripheral edge portions 1b of the respective leg-openings 15 to form a plurality of gathers. Contraction of the elastic members 12 causes the free side edge portions 5b of the respective leak-barrier cuffs 5 to rise on the topsheet 2 and contraction of the elastic member 13 causes the free end portion 8b of the leak-barrier cuff 8 to rise on the cover sheet 6.

Figure 3:
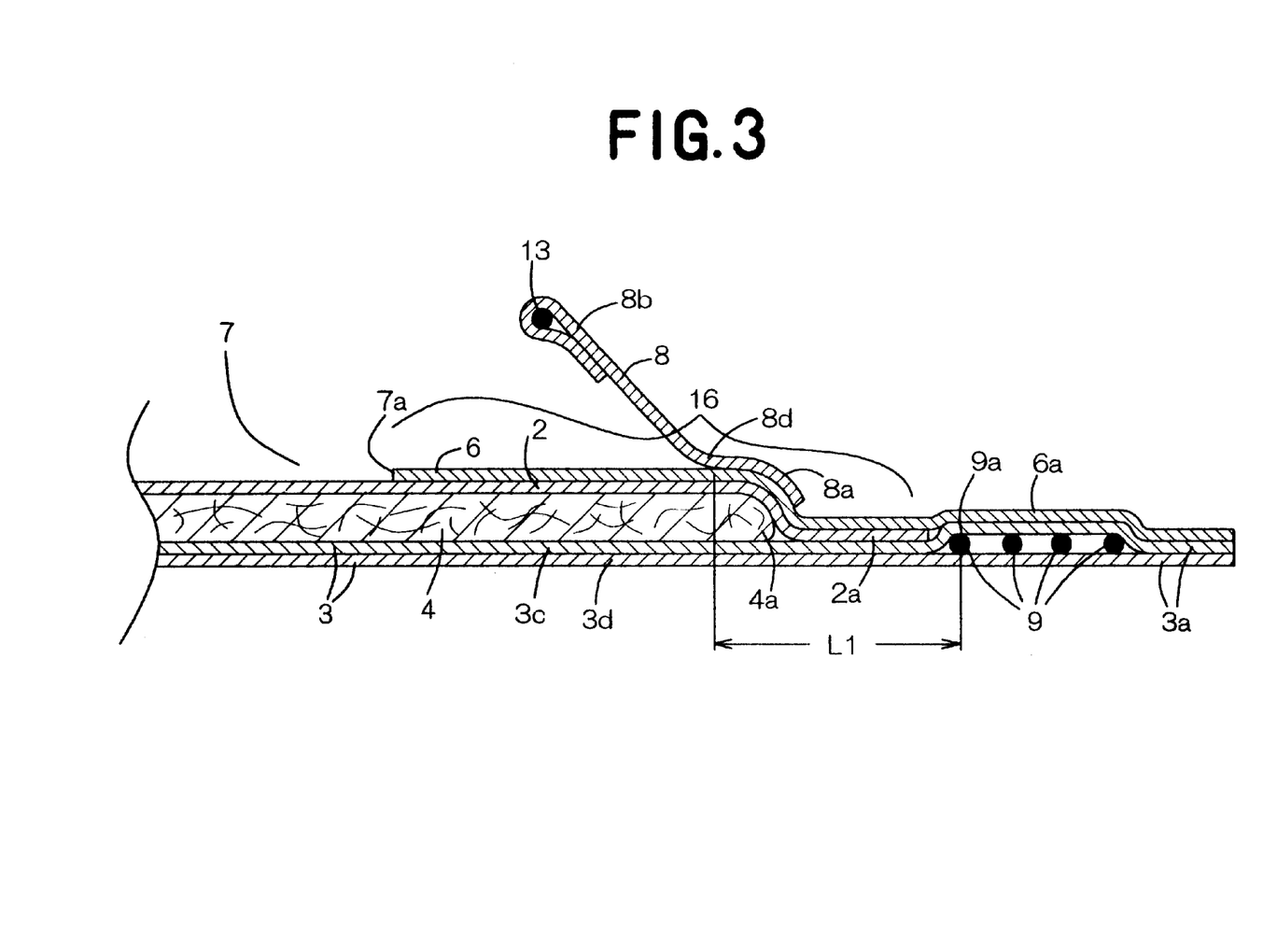
FIG. 3 is a sectional view taken along a line A—A in FIG. 2.
Figure 4:
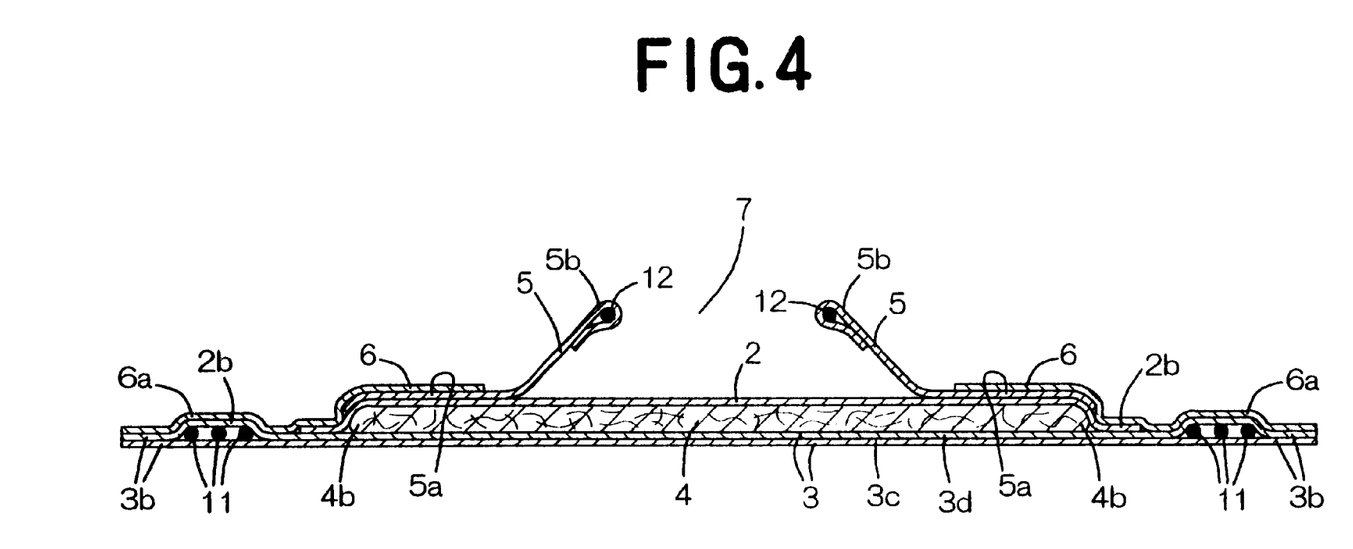
FIG. 4 is a sectional view taken along a line B—B in FIG. 2.

FIG. 3 is a sectional view taken along a line A—A in FIG. 2 and FIG. 4 is a sectional view taken along a line B—B in FIG. 2. In the rear waist region 22 of the diaper 1, the fixed end portion 8a of the leak-barrier cuff 8 is spaced apart from the elastic member 9 associated with the waist-opening toward the crotch region 21 by a given dimension, as seen in FIG. 3. Of the leak-barrier cuff 8, a fulcrum zone 8d along which this cuff 8 is elastically biased to rise lies on a substantially non-contractible region 16 of the cover sheet 6 extending between the elastic member 9 associated with the waist-opening and the elastic members 11 associated with the leg-openings. Contraction of the elastic member 9 associated with the peripheral edge portion 1a of the waist-opening 14 in the waist-surrounding direction does not result in contraction of the free end portion 8b of the leak-barrier cuff 8, i.e., none of creases or gathers is generated along this free end portion 8b.

In the diaper 1, the fixed end portion 8a and the rising fulcrum zone 8d of the leak-barrier cuff 8 lie on the outer surface of the cover sheet 6 covering the core 4 in the vicinity of its one longitudinal end 4a. Such unique arrangement ensures that the core 4 having a stiffness higher than those of the top- and backsheets 2, 3 and the cover sheet 6 can prevent the free end portion 8b of the leak-barrier cuff 8 from contracting. An alternative arrangement is possible such that the fixed end portion 8a and the rising fulcrum zone 8d lie on the outer surface of the cover sheet 6 extending between the longitudinal end 4a of the core 4 and the elastic member 9 associated with the waist-opening.

The rising fulcrum zone 8d of the leak-barrier cuff 8 is spaced apart from the one element 9a of the elastic member 9 associated with the waist-opening lying adjacent the rising fulcrum zone 8d by a dimension L1 of 5~15 mm. If this dimension L1 is less than 5 mm, the free end portion 8b of the leak-barrier cuff 8 would contract and form gathers as the elastic member 9 associated with the waist-opening contracts.

In the vicinity of the longitudinal end 1a of the rear waist region 22, the longitudinal end portion 2a of the topsheet 2 extends outward slightly beyond the longitudinal end 4a of the core 4. The longitudinal end portion 3a of the backsheet 3 and a peripheral edge portion 6a of the cover sheet 6 extend outward beyond the longitudinal end portion 2a of the topsheet 2. The end portion 2a is disposed between the end portion 3a and the peripheral edge portion 6a and bonded to these end portion 3a and peripheral edge portion 6a. The end portion 3a is bonded to the peripheral edge portion 6a along a zone in which these two portions 3a, 6a are placed upon each other.

The backsheet 3 is formed with a composite sheet made of a plastic film 3c and a hydrophobic nonwoven fabric 3d laminated with the plastic film 3c with the elastic member 9 associated with the waist-opening disposed between these plastic film 3c and hydrophobic nonwoven fabric 3d.

In the vicinity of the longitudinal end portion 1a of the rear waist region 22 defining the peripheral edge portion 1a of the waist-opening 14, the free end portion 8b of the leak-barrier cuff 8 rises to form a barrier. Even if excretion discharged on the diaper 1 leaks beyond a peripheral edge 7a of the opening 7 onto the outer surface of the cover sheet 6, the free end portion 8b of the leak-barrier cuff 8 reliably prevents excretion from further spreading and thereby prevents excretion from leaking beyond the peripheral edge portion 1a of the waist-opening 14. The longitudinal end 2a of the topsheet 2 does not extend to the outermost edge of the peripheral edge portion 1a and therefore it is not apprehended that any amount of excretion having reached the longitudinal end 2a might leak out beyond the peripheral edge portion 1a.

As will be seen in FIG. 4, in the vicinity of the peripheral edge portions 1b of the respective leg-openings 15, transversely opposite side edge portions 2b of the topsheet 2 extending outward slightly beyond the respective side edges 4b of the core 4 and transversely opposite side edge portions 3b of the backsheet 3 as well as the peripheral edge portion 6a of the cover sheet 6 extend further outward beyond the side edge portions 2b of the topsheet 2. The side edge portions 2b are disposed between and bonded to the side edge portions 3b and the peripheral edge portion 6a. The side edge portions 3b and the peripheral edge portion 6a are bonded to together in a zone along which these two portions 3b, 6a are placed upon each other. The respective elastic members 11 associated with the leg-openings are disposed and bonded between the plastic film 3c and the hydrophobic nonwoven fabric 3d forming the backsheet 3. In the crotch region 21, the free side edge portions 5b of the respective leak-barrier cuffs 5 rise to form barriers adapted to avoid an anxiety that any amount of excretion might leak from the crotch region 21. In the vicinity of the peripheral edge portions 1b of the respective leg-openings 15, the transversely opposite side edge portions 2b of the topsheet 2 do not extend to the outermost edges of the respective peripheral edge portions 1b so that an amount of excretion having reached the transversely opposite side edge portions 2b can no more flow beyond the peripheral edge portions 1b of the respective leg-openings 15.

Alternatively, it is possible to attach the leak-barrier cuff 8 to the outer surface of the cover sheet 6 in the front waist region 20. In this case, the rising fulcrum zone 8d for the leak-barrier cuff 8 must lie in a substantially non-contractile region 17 (See FIG. 1) of the cover sheet 6 extending between the elastic member 10 associated with the waist-opening and the elastic members 11 associated with the leg-openings.

Figure 5:
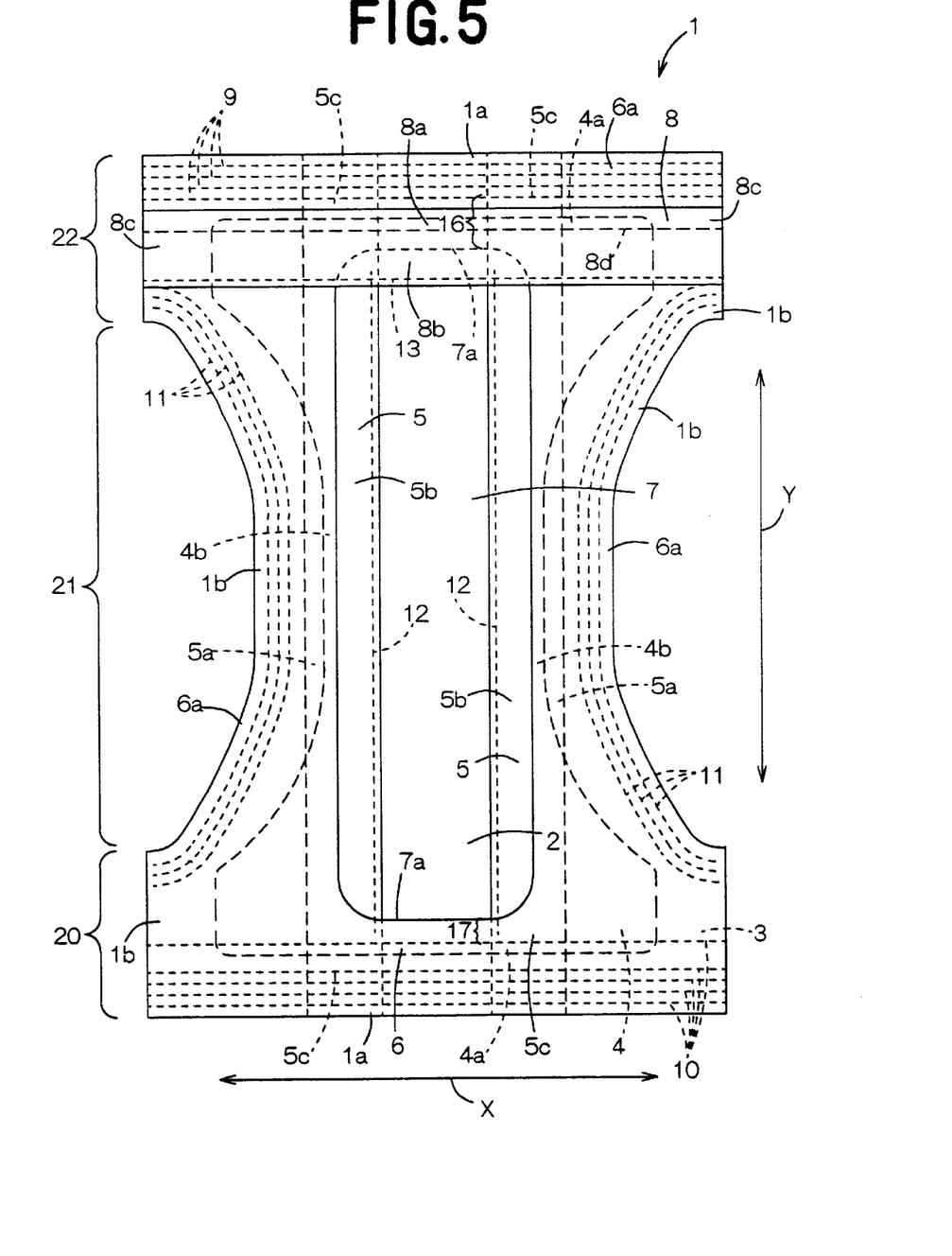
FIG. 5 is a plan view showing another embodiment of the diaper.
Figure 6:
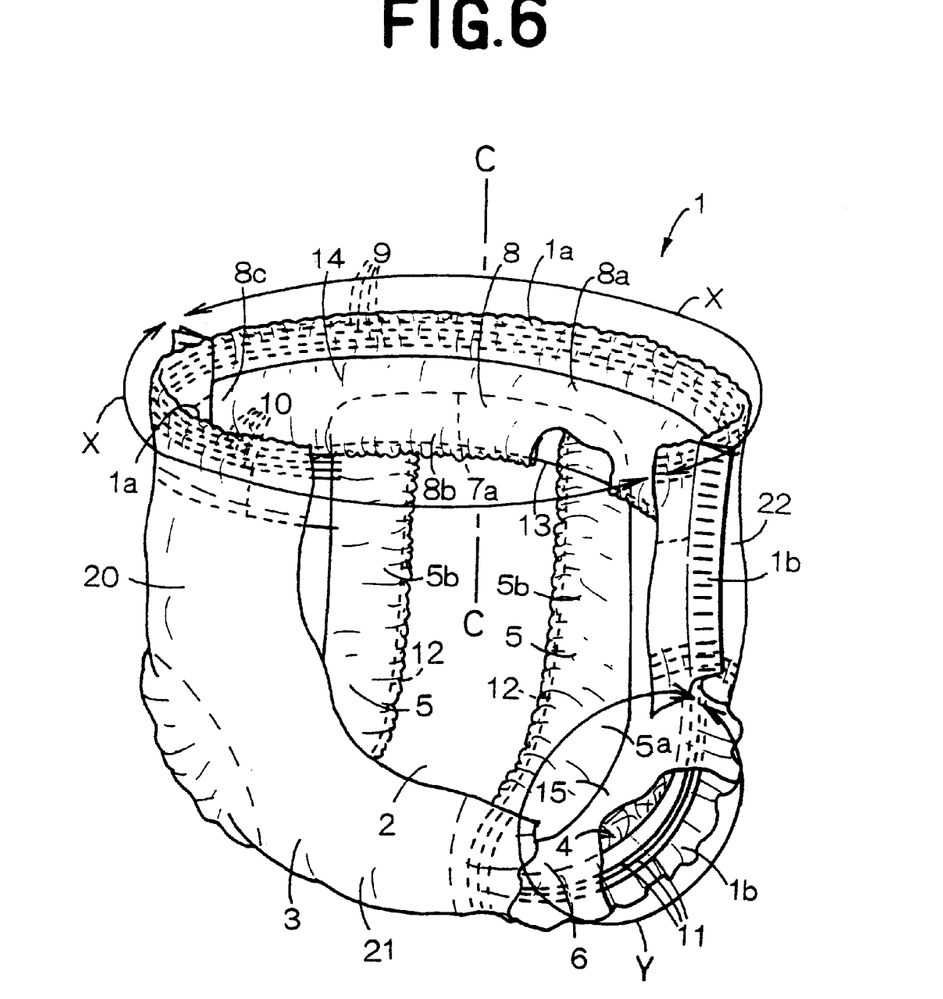
FIG. 6 is a perspective view showing the pants-type diaper obtained from the state shown in FIG. 5 as partially broken away.
Figure 7:
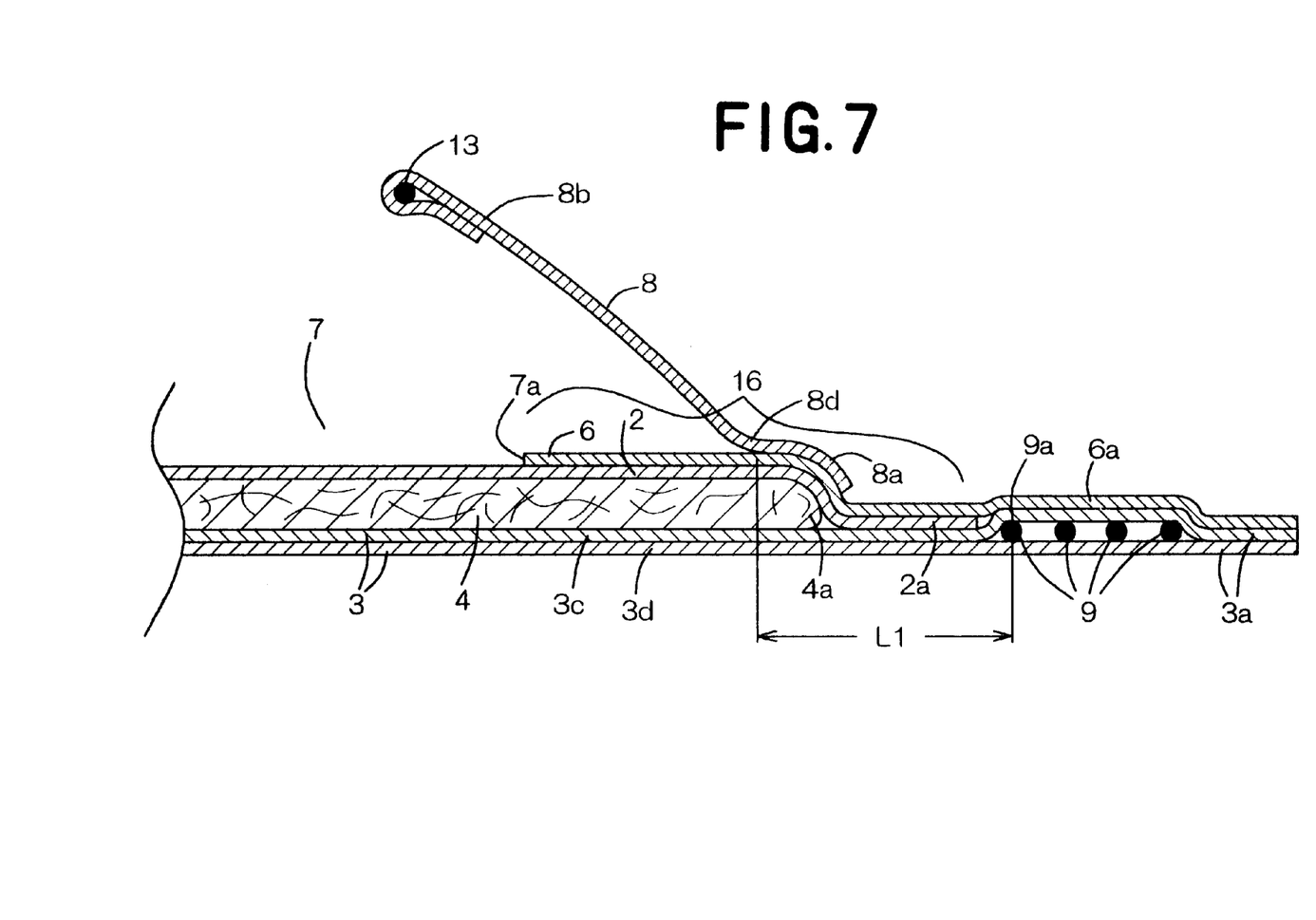
FIG. 7 is a sectional view taken along a line C—C in FIG. 6.

FIG. 5 is a plan view showing another embodiment of the diaper 1, FIG. 6 is a perspective view showing this diaper 1 shaped into pants-type diaper 1 as partially broken away and FIG. 7 is a sectional view taken along a line C—C in FIG. 6. Similarly to the diaper 1 of FIG. 2, this diaper 1 comprises the liquid-pervious topsheet 2, the liquid-impervious backsheet 3, the liquid-absorbent core 4 disposed between the top- and backsheets 2, 3, a pair of substantially liquid-impervious leak-barrier cuffs 5 associated with leg-openings, substantially liquid-impervious the cover sheet 6 and a leak-barrier cuff 8 associated with a waist-opening. The diaper 1 of FIG. 5 is different from the diaper 1 of FIG. 2 in features as will be described.

In this diaper 1, the central opening 7 of the cover sheet 6 extends across a substantially entire area of the crotch region 21 and further extends into the front and rear waist regions 20, 22 to mid levels thereof. The free end portion 8b of the leak-barrier cuff 8 extends above the opening 7 in the rear waist region 22.

In this diaper 1, a longitudinal dimension of the opening 7 is larger than that of the diaper 1 shown in FIG. 1 so that an exposed area of the topsheet 2 can be enlarged and thereby excretion can be reliably received in the opening 7. In the case of this diaper 1, the free end portion 8b of the leak-barrier cuff 8 partially covers the opening 7 from above as the free end portion 8b rises to form the barrier. Such unique arrangement ensures that, even if excretion spreading on the outer surface of the topsheet is concentrated around the peripheral edge portion 1a of the waist-opening 14 in the rear waist region 22, the free end portion 8b of the leak-barrier cuff 8 serves as the barrier adapted to eliminate an anxiety that excretion might leak out from the peripheral edge portion 1a of the waist-opening 14.

Figure 8:
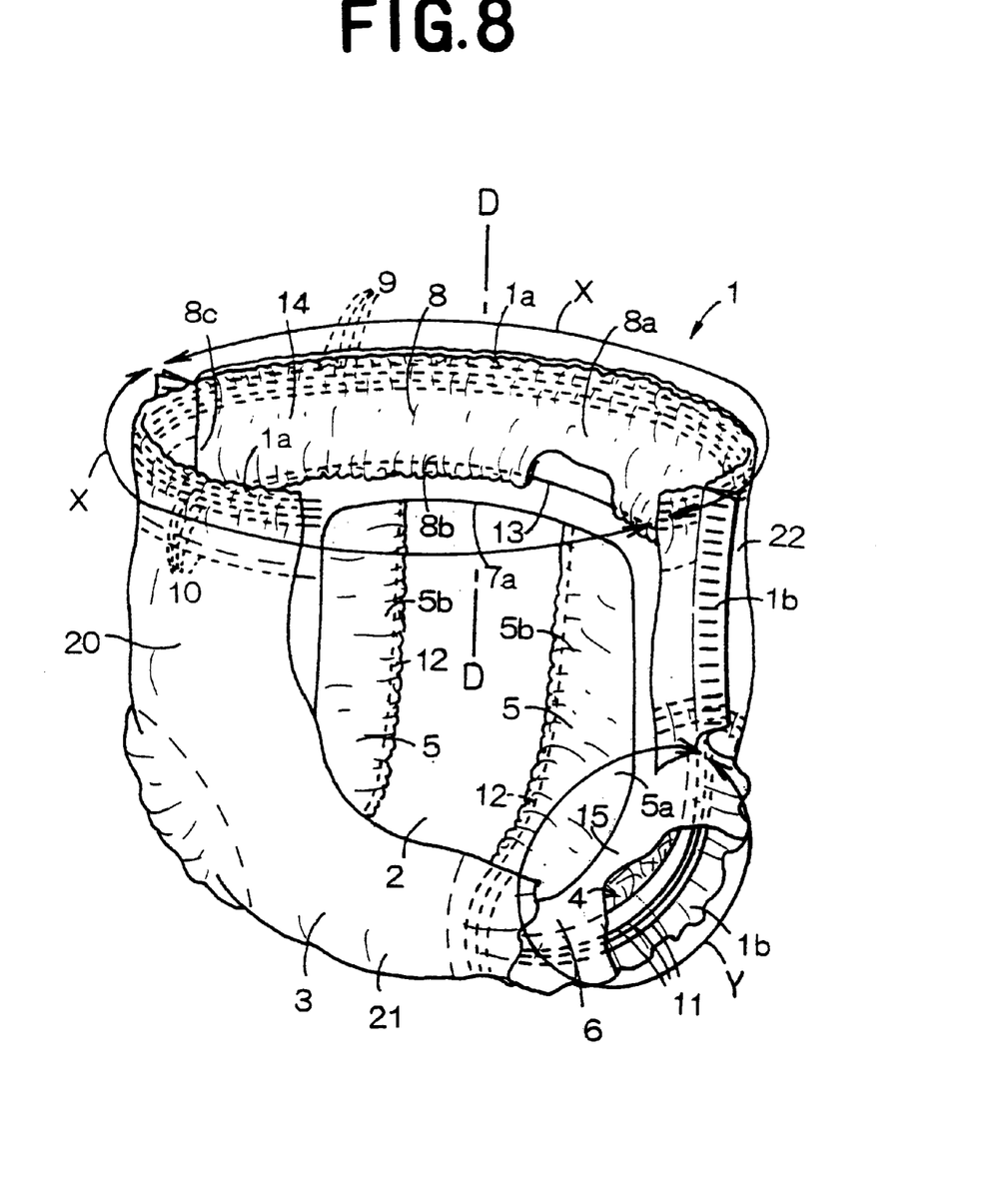
FIG. 8 is a perspective view showing still another embodiment of the pants-type diaper as partially broken away.
Figure 9:
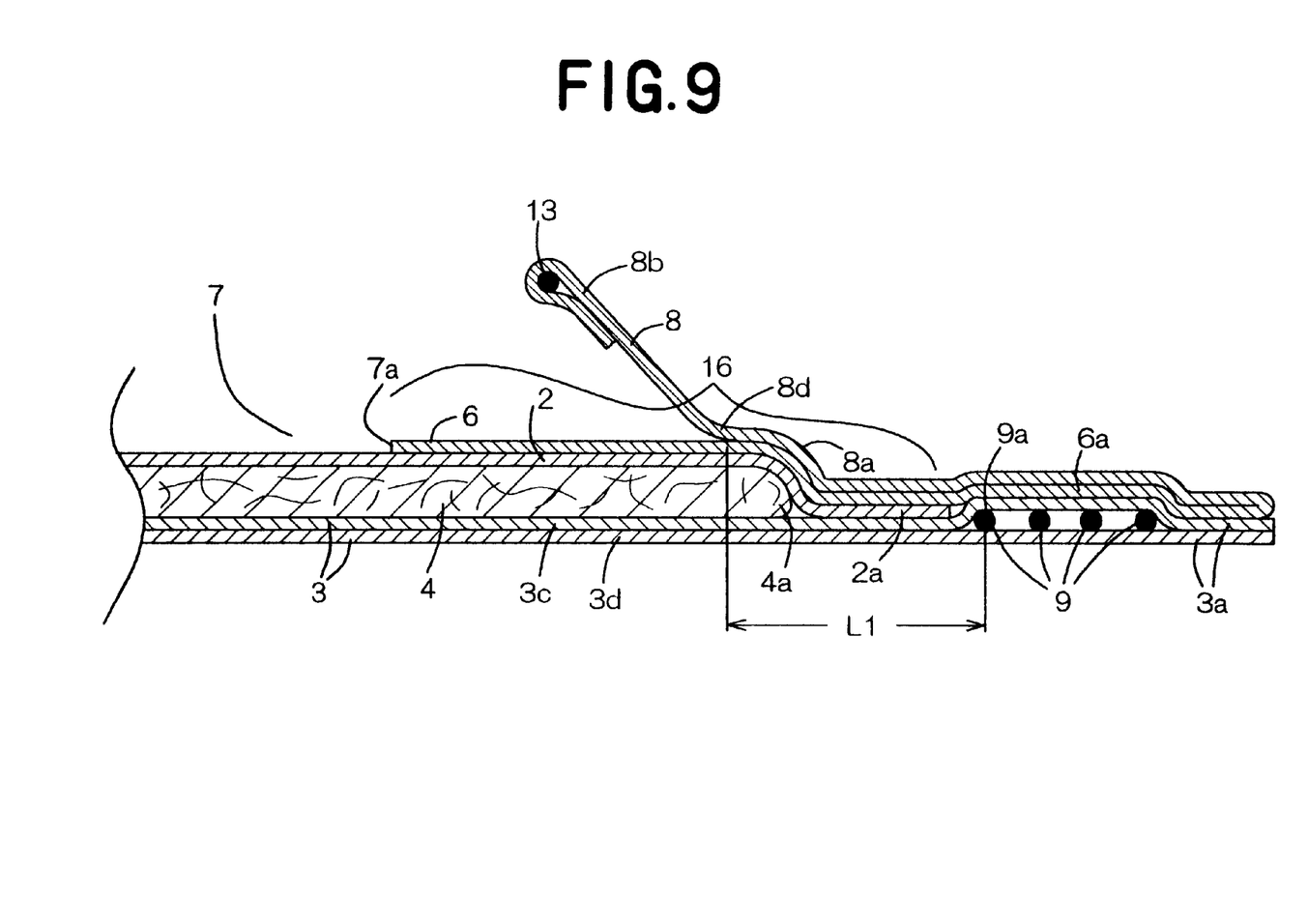
FIG. 9 is a sectional view taken along a line D—D in FIG. 8.

FIG. 8 is a perspective view showing still another embodiment of the pants-type diaper 1 and FIG. 8 is a sectional view taken along a line D—D. In this diaper 1, a part of the cover sheet 6 serves also as the leak-barrier cuff 8 associated with the waist-opening. This leak-barrier cuff 8 is defined by the part of the cover sheet 6 extending outward from the peripheral edge portion 1a of the waist-opening 14 in the rear waist region 22 and folded back along the peripheral edge portion 1a onto the outer surface of the cover sheet 6.

Figure 10:
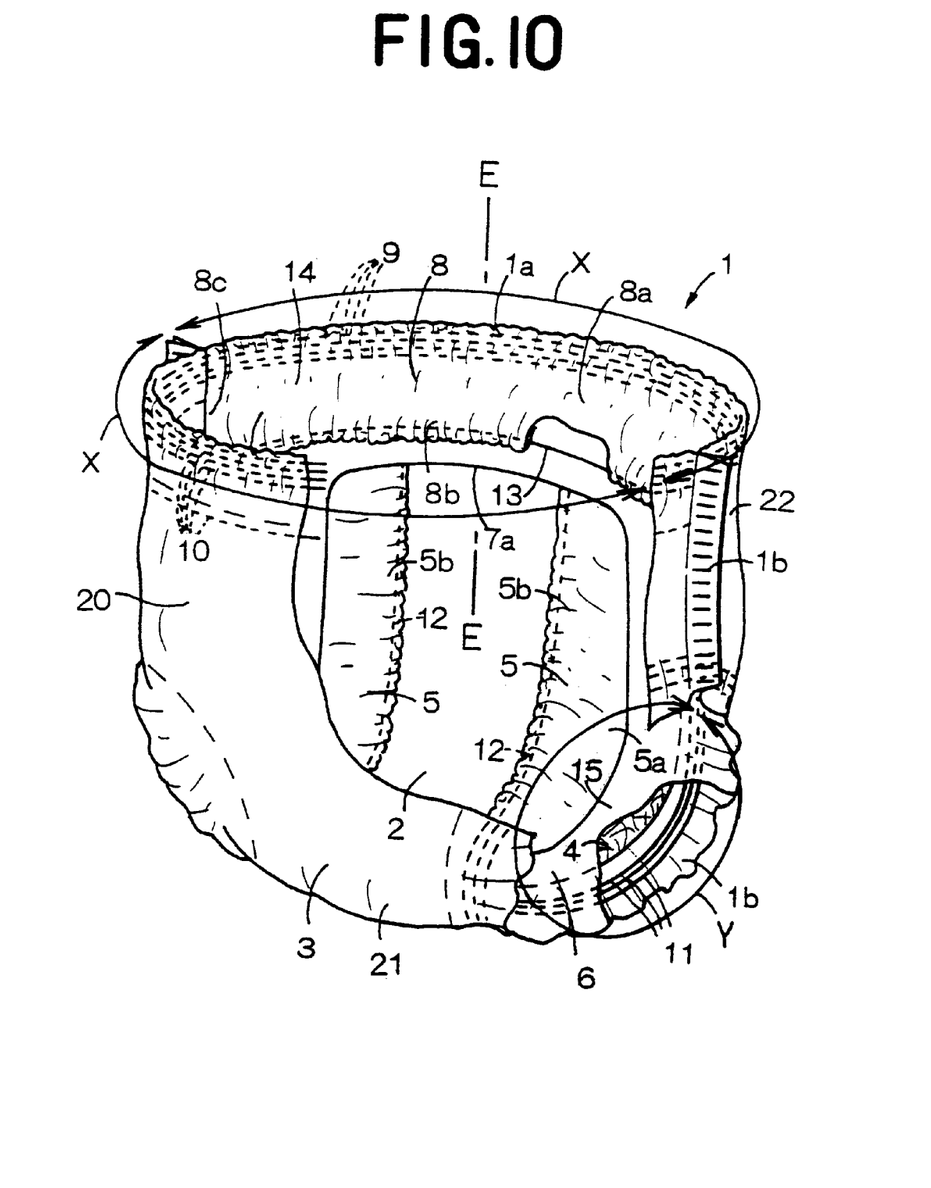
FIG. 10 is a perspective view showing further another embodiment of the pants-type diaper as partially broken away.
Figure 11:
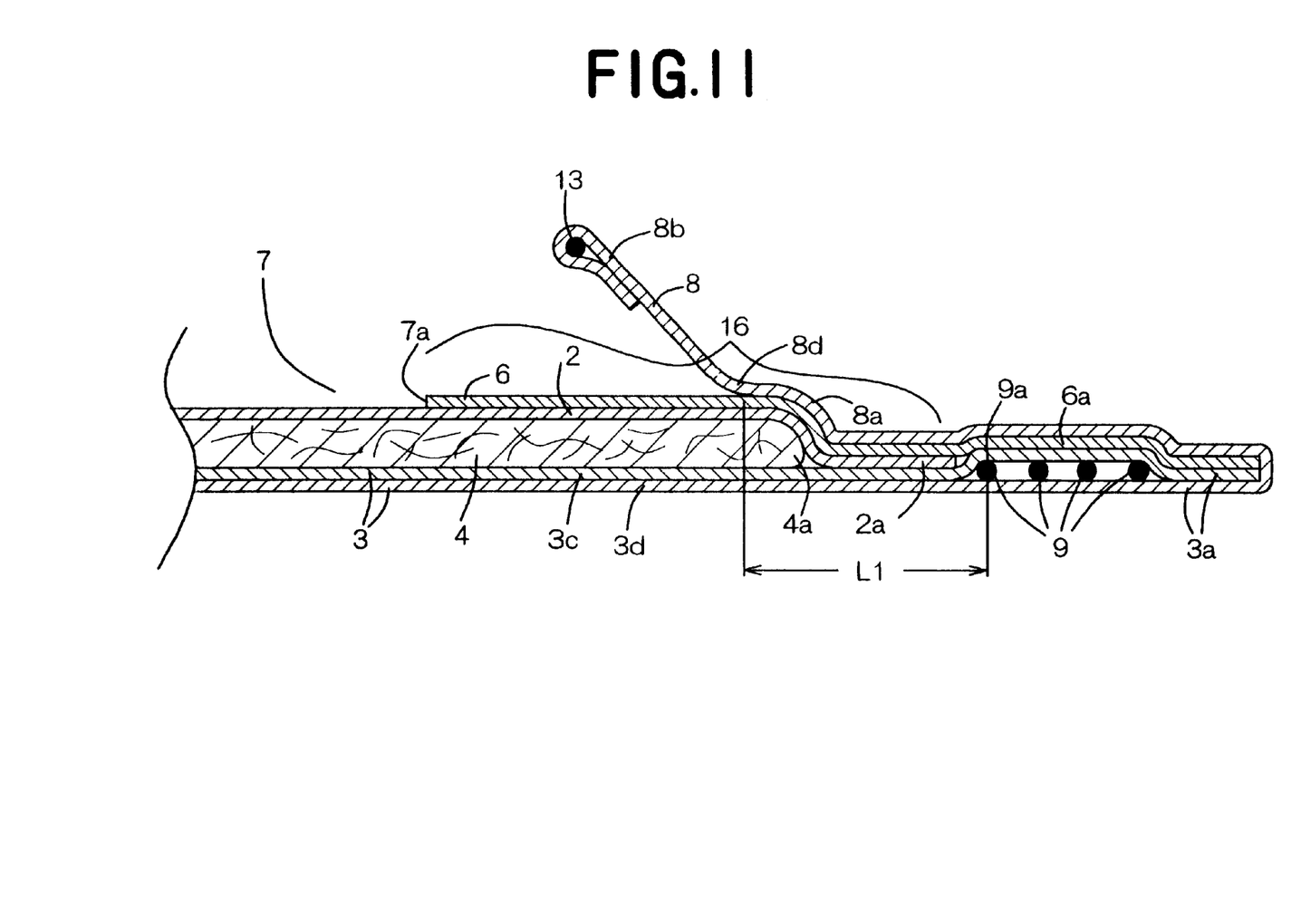
FIG. 11 is a sectional view taken along a line E—E in FIG. 10.

FIG. 10 is a perspective view showing still another embodiment of the pants-type diaper 1 as partially broken away and FIG. 11 is a sectional view taken along a line E—E in FIG. 10. In this diaper 1, a part of the hydrophobic nonwoven fabric 3d forming the backsheet 3 serves also as the leak-barrier cuff 8 associated with the waist-opening. This leak-barrier cuff 8 is defined by the part of the hydrophobic nonwoven fabric 3d extending outward from the peripheral edge portion 1a of the waist-opening 14 in the rear waist region 22 and folded back along the peripheral edge portion 1a onto the outer surface of the cover sheet 6.

So far as the diaper 1 shown in FIGS. 5, 8 and 10 is concerned, the rising fulcrum zone 8d of the leak-barrier cuff 8 lies on the substantially non-contractible region 16 of the cover sheet 6 extending between the elastic member 9 associated with the waist-opening and the elastic members 11 associated with the leg-openings. The rising fulcrum zone 8d of the leak-barrier cuff 8 is spaced apart from the innermost one 9a of the elastic elements constituting the elastic member 9 associated with the waist-opening lying adjacent the zone 8d preferably by a dimension L1 of 5~15 mm.

The topsheet 2 may be formed from a liquid-pervious sheet such as a nonwoven fabric or a porous plastic film. The backsheet 3 may be formed from a hydrophobic nonwoven fabric, liquid-impervious plastic film or a laminated sheet of a hydrophobic nonwoven fabric and plastic film. The leak-barrier cuffs 5, the cover sheet 6 and the leak-barrier cuff 8 may be formed from a composite nonwoven fabric consisting of a melt blown nonwoven fabric having a high water-resistance and two layers of spun bond nonwoven fabric having high strength and flexibility sandwiching the melt blown nonwoven fabric.

The nonwoven fabric may be selected from a group including spun lace-, needle punch-, melt blown-, thermal bond-, spun bond-, chemical bond- and air through-nonwoven fabric. Component fibers of the nonwoven fabric may be selected from a group including polyolefine-, polyester- and polyamide-based fibers and polyethylene/polypropylene or polyethylene/polyester core-sheath type conjugated fiber and side-by-side-type conjugated fibers.

The core 4 is a mixture of fluff pulp, high absorption polymer particles and thermoplastic synthetic resin fiber compressed to a desired thickness. Therefore, the core 4 has a stiffness higher than those of the top- and backsheets 2, 3 and the cover sheet 6. The polymer grains may be selected from a group including starch-, cellulose-based polymer and synthetic polymer.

To bond the top- and backsheets 2, 3 to each other, to bond the leak-barrier cuffs 5, the cover sheet 6 and the leak-barrier cuff 8 to the top- and backsheets 2, 3 and to bond the core 4 to the top- and backsheets 2, 3 and to attach the elastic members 9, 10, 11, 12, 13 to the diaper 1, suitable adhesive such as hot melt adhesive or welding means such as heat-sealing or ultrasonic sealing may be used.

This invention may be also implemented in the form of an open-type diaper having its front and rear waist regions connected to each other through engagement between tape fasteners and a target tape strip.

The disposable wearing article according to this invention has a rising fulcrum zone of the leak-barrier cuff associated with the waist-opening which lies in the substantially non-contractible region of the article extending between the elastic member associated with the waist-opening and the elastic members associated with the leg-openings. This unique arrangement ensures that contraction of the elastic member associated with the waist-opening does not cause the free end portion of the leak-barrier cuff to contract and to be creased. Consequently, it is not apprehended that the free end portion of the leak-barrier cuff might be partially collapsed toward the topsheet and reliably rises to form the barrier adapted to eliminate an anxiety that any amount of excretion might leak from the longitudinally opposite end portions of the article.

In the article according to this invention implemented in the manner that the opening of the cover sheet extends across the crotch region further into any one waist region and the free end portion of the leak-barrier cuff extends above the opening of the cover sheet in this waist region, excretion discharged on the article can be reliably received in the opening of the cover sheet. In addition, the free end portion of the leak-barrier cuff covers a part of the opening so that even if the amount of excretion spreading on the outer surface of the topsheet tends to be concentrated to the longitudinally opposite end portions of the article, the free end portion of the leak-barrier cuff functions as the barrier adapted to eliminate the anxiety that any amount of excretion might leak from the longitudinally opposite end portions of the article.

What is claimed is:
1. A disposable wearing article comprising:
   a liquid-pervious topsheet;

a liquid-impervious backsheet;

a liquid-absorbent core positioned between said liquid-pervious to sheet and said liquid-impervious backsheet;

a front waist region;

a rear waist region;

a crotch region extending between said front and rear waist regions;

longitudinally opposite end portions extending in parallel to each other in a first direction across said front and rear waist regions;

transversely opposite side edge portions extending between said longitudinally opposite end portions in a second direction;

elastic members being stretchable in said first direction attached under tension to said longitudinally opposite end portions so as to be adjacent a waist-opening;

elastic members being stretchable in said second direction attached under tension to said transversely opposite side edge portions in said crotch region so as to be adjacent a pair of leg-openings; and a substantially liquid-impervious leak-barrier cuff adjacent the waist-opening extending in said first direction across at least said rear waist region of said front and rear waist regions, said leak-barrier cuff having:

a fixed end portion lying adjacent one longitudinal end portion of said article;

a free end portion extending from said fixed end portion toward the crotch region;

fixed side portions lying on respective ones of said transversely opposite side edge portions;

an elastic member being stretchable in said first direction is attached under tension to said free end portion so that said free end portion is biased by said elastic member to rise on said topsheet; and a rising fulcrum zone of said leak-barrier cuff that lies in a substantially non-contractible region of said article extending between said elastic member adjacent the waist-opening and said elastic member adjacent the leg-openings, wherein said leak-barrier cuff is defined by a part of said backsheet that extends outward from a longitudinally opposite end portion of said article in the second direction and is folded back along said longitudinally opposite end portions toward an outer surface of said topsheet.

2. The article according to claim 1, wherein a substantially liquid-impervious cover sheet having a central opening which is elongated in said second direction is provided on an outer surface of said topsheet and bonded to said longitudinal opposite end portions and to transversely opposite side edge portions, and wherein said leak-barrier cuff extends on an outer surface of said cover sheet in said first direction so that said free end portion of said leak-barrier cuff farina a barrier that rises on said cover sheet.

3. The article according to claim 2, wherein the opening of said sheet extends across said crotch region and further extends into said front and rear waist regions so that the free end portion of said leak-barrier cuff extends above said opening in said front and rear waist regions.

4. The article according to claim 1, wherein said rising fulcrum zone of said leak-barrier cuff is spaced apart from said elastic member adjacent the waist-opening by a dimension of about 5 to about 15 mm.

5. The article according to claim 1, wherein said rising fulcrum zone of said leak-barrier cuff lies in a vicinity of a longitudinal end of said liquid-absorbent core and extends between the transversely opposite side edge portions of said article.

* * * * *